United States Patent
Ciavarini et al.

(10) Patent No.: US 11,887,700 B2
(45) Date of Patent: Jan. 30, 2024

(54) TECHNIQUES FOR GENERATING ENCODED REPRESENTATIONS OF COMPOUNDS

(71) Applicant: WATERS TECHNOLOGIES IRELAND LIMITED, Dublin (IE)

(72) Inventors: Steven J. Ciavarini, Natick, MA (US); Curt Devlin, Fairhaven, MA (US); Patrick Brophy, Newton Highlands, MA (US); Scott J. Geromanos, Middletown, NJ (US)

(73) Assignee: WATERS TECHNOLOGIES IRELAND LIMITED, Dublin (IE)

( * ) Notice: Subject to any disclaimer, the term of this patent is extended or adjusted under 35 U.S.C. 154(b) by 272 days.

(21) Appl. No.: 16/865,880

(22) Filed: May 4, 2020

(65) Prior Publication Data
US 2020/0350039 A1  Nov. 5, 2020

Related U.S. Application Data

(60) Provisional application No. 62/842,694, filed on May 3, 2019.

(51) Int. Cl.
*G16C 20/20* (2019.01)
*G16C 20/80* (2019.01)
*G01N 30/00* (2006.01)

(52) U.S. Cl.
CPC ............. *G16C 20/20* (2019.02); *G01N 30/00* (2013.01); *G16C 20/80* (2019.02)

(58) Field of Classification Search
CPC ........ G01N 30/00; G16C 20/20; G16C 20/40; G16C 20/80; H01J 49/0036
See application file for complete search history.

(56) References Cited

U.S. PATENT DOCUMENTS

2003/0113797 A1* 6/2003 Jia ...................... G01N 33/5097
435/7.1
2005/0061056 A1* 3/2005 Sunshine ........... G01N 33/0073
73/23.2
(Continued)

FOREIGN PATENT DOCUMENTS

WO   WO-2016196432 A1 * 12/2016 ........... G01N 27/622
WO   2019079492 A1   4/2019

OTHER PUBLICATIONS

Grotch, Computer Identification of Mass Spectra Using Highly Compressed Spectral Codes, Analytical Chemistry, vol. 45, No. 1, Jan. 1973 (Year: 1973).*

International Search Report and Written Opinion for International applicaiton No. PCT/IB2020/054224, dated Sep. 17, 2020, 14 pages.

(Continued)

*Primary Examiner* — Michael J Dalbo
(74) *Attorney, Agent, or Firm* — Goodwin Procter LLP (57) ABSTRACT

Techniques and apparatus for generating encoded representations of compounds are described. In one embodiment, for example, an apparatus may include at least one memory, and logic coupled to the at least one memory. The logic may be configured receive analytical information associated with at least one compound, generate at least one encoded representation of the at least one compound, the encoded representation comprising at least one segment representing at least one property of the at least one compound using a plurality of symbols. Other embodiments are described.

18 Claims, 10 Drawing Sheets

(56) References Cited

U.S. PATENT DOCUMENTS

| | | | | |
|---|---|---|---|---|
| 2012/0085905 A1* | 4/2012 | Satoh | .................. | H01J 49/004 250/287 |
| 2012/0115740 A1* | 5/2012 | Ehrlich | ............... | C12Q 1/6827 435/6.15 |
| 2012/0158318 A1* | 6/2012 | Wright | ................... | G01N 15/02 702/28 |
| 2014/0138537 A1* | 5/2014 | Grothe, Jr. | ............. | H01J 49/26 250/282 |
| 2014/0316718 A1* | 10/2014 | Crowell | ............ | H01J 49/0036 702/32 |
| 2015/0090872 A1* | 4/2015 | Platt | ....................... | H03M 7/40 250/281 |
| 2016/0379100 A1* | 12/2016 | Brylev | ................... | G06K 19/02 235/494 |
| 2018/0308673 A1 | 10/2018 | Platt et al. | | |
| 2019/0303450 A1* | 10/2019 | Richards | ............ | G06F 16/3331 |

OTHER PUBLICATIONS

Borland, L., et al., "Review of chemical signature databases", Analytical and Bionanalytical Chemistry, 397 (3):1019-1028 (2010).

Dettmer, K., et al., "Mass spectrometry-based metabolomics", Mass Spectrometry Reivews 26(1):51-78 (2007).

Deutsch, E.W., et al., "File Formats Commonly Use in Mass Spectrometry Proteomics", Molecular and Cellular Proteomics 11(12):1612-1621 (2012).

Merritt, C., et al., "Combined gas chromatography-mass spectrometry-computer system for the analysis of volatile components of foods" Journal of Agricultural and Food Chemistry 22(5):750-755 (1974).

Neumann, S., et al., "Computational mass spectrometry for metabolomics: Identification of metabolites and small molecules" Analytical and Bionanalytical Chemistry 398(7-8):2779-2788 (2010).

Examination Report (Communication Pursuant to Article 94(3) EPC) for European Patent Application No. 20724952.5, dated Sep. 1, 2023.

* cited by examiner

TECHNIQUES FOR GENERATING ENCODED REPRESENTATIONS OF COMPOUNDS

CROSS-REFERENCE TO RELATED APPLICATIONS

This application claims the benefit of and priority to U.S. Provisional Patent Application No. 62/842,694, filed on May 3, 2019, the entire contents of which are incorporated by reference.

TECHNICAL FIELD

Embodiments herein generally relate to mass analysis of a sample and, more particularly, to generating and using encoded representations for identifying compounds in a sample.

BACKGROUND

Mass analysis techniques, such as mass spectrometry (MS) or liquid chromatography mass spectrometry (LC-MS), are used to identify and/or quantify molecular species in a sample. During analysis, molecules from a sample are ionized to acquire a charge and are then introduced as ions into a mass analyzer. The mass analyzer determines analytical information associated with the ions based on characteristics of the ions, such as their mass-to-charge ratio (m/z). A detector produces a signal relating to the intensity of the ions at their particular m/z. The identification of sample components in a conventional mass analysis experiment involves matching the analytical information with models, libraries, and/or the like of known compounds (e.g., "compound libraries"). Non-limiting examples of compound libraries for MS analyses may include NIST and METLIN databases. The analytical information and the compound libraries are generally complex and high-resolution data. Accordingly, conventional techniques for determining compounds of interest in a sample, particularly a complex sample, are inefficient and time-consuming processes. As a result, real-time or near real-time analysis of complex samples is not possible using current methods.

DETAILED DESCRIPTION

Various embodiments may generally be directed toward systems, methods, and/or apparatus for generating encoded representations of compounds. In general, a compound may be or may include a molecule, a molecule fragment, a precursor molecule, a product molecule, and/or the like. In some embodiments, an encoded representation may include an information element formed of symbols configured to represent properties of a compound. In various embodiments, an encoded representation may include a string of alphanumeric characters. In exemplary embodiments, the encoded representations may include binary characters (for instance, 1 s and 0 s), such as a string of binary characters, with at least a portion of the binary characters set to a particular binary value. In some embodiments, the properties represented in an encoded representation may include, without limitation, mass (m), charge (z), mass-to-charge ratio (m/z), retention time, drift time, collisional cross-sectional area (CCS $A^2$), and/or the like. In exemplary embodiments, an encoded representation may include discrete character segments, with one or more of the character segments being associated with a particular property.

In this manner, high-resolution processes (for instance, MS, tandem MS, and/or the like) may be used to create encoded representations of molecular species in a sample. The encoded representations may be or may encompass low-resolution versions of the corresponding high-resolution library information. The encoded representations generated according to some embodiments may be used as targets to identify and/or quantify molecular species in a sample using either high-resolution or low-resolution instrumentation. In this manner, the use of low-resolution instrumentation to conduct mass analysis according to some embodiments may be more efficient and require less processing resources to identify and/or quantify sample constituents compared with conventional methods.

In this description, numerous specific details, such as component and system configurations, may be set forth in order to provide a more thorough understanding of the described embodiments. It will be appreciated, however, by one skilled in the art, that the described embodiments may be practiced without such specific details. Additionally, some well-known structures, elements, and other features have not been shown in detail, to avoid unnecessarily obscuring the described embodiments.

In the following description, references to "one embodiment," "an embodiment," "example embodiment," "various embodiments," etc., indicate that the embodiment(s) of the technology so described may include particular features, structures, or characteristics, but more than one embodiment may and not every embodiment necessarily does include the particular features, structures, or characteristics. Further, some embodiments may have some, all, or none of the features described for other embodiments.

As used in this description and the claims and unless otherwise specified, the use of the ordinal adjectives "first," "second," "third," etc. to describe an element merely indicate that a particular instance of an element or different instances of like elements are being referred to, and is not intended to imply that the elements so described must be in a particular sequence, either temporally, spatially, in ranking, or in any other manner.

Figure 1:
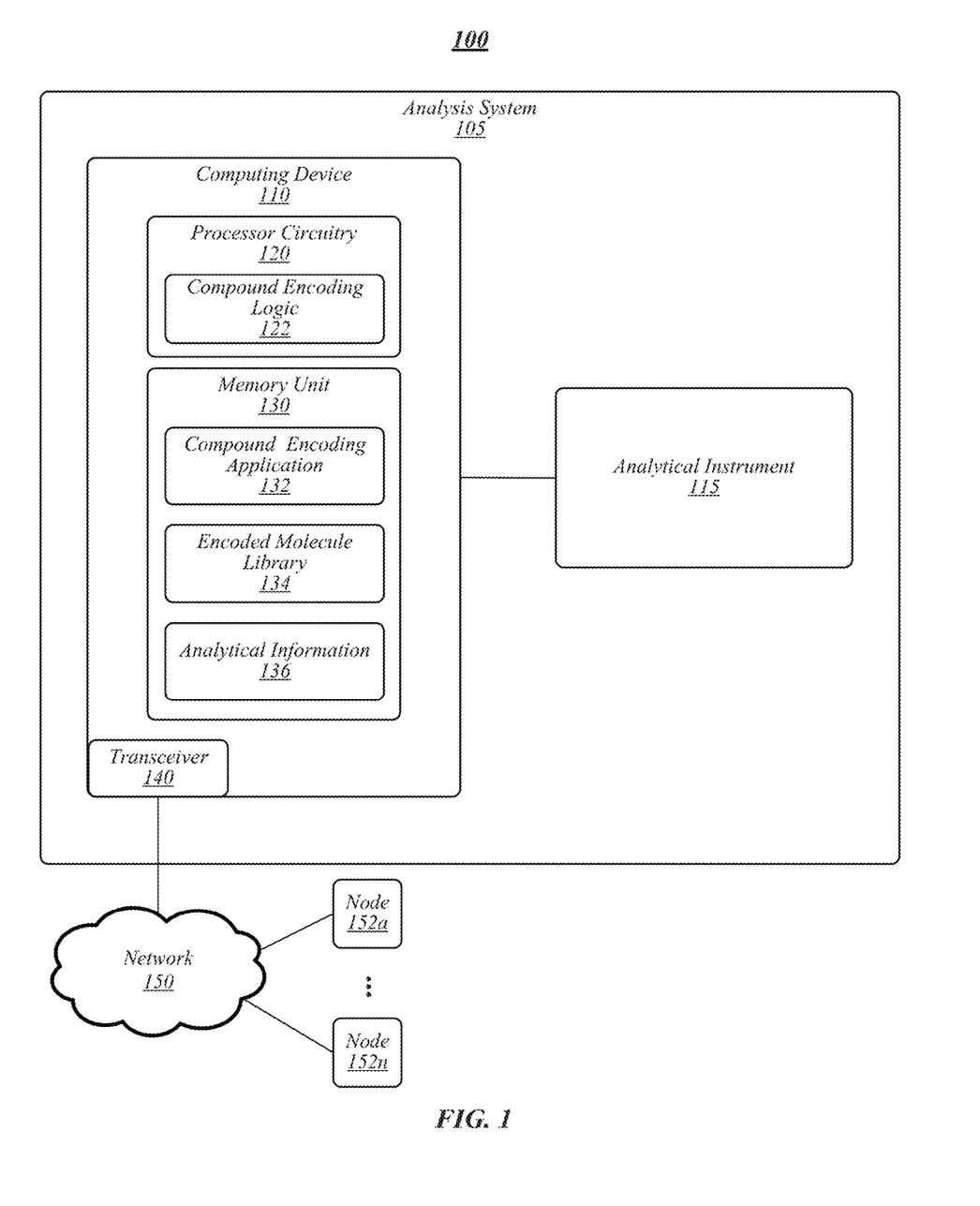
FIG. 1 illustrates an embodiment of a first operating environment.

FIG. 1 illustrates an example of an operating environment 100 that may be representative of some embodiments. As shown in FIG. 1, operating environment 100 may include an analysis system 105 operative to manage analytical information associated with analytical instrument 115. In some embodiments, analytical instrument 115 may be or may include a chromatography system, a liquid chromatography (LC) system, a gas chromatography (GC) system, a mass analyzer system, a mass detector system, a mass spectrometer (MS) system, an ion mobility spectrometer (IMS) system, a high-performance liquid chromatography (HPLC) system, a ultra-performance liquid chromatography (UPLC®) system, a ultra-high performance liquid chromatography (UHPLC) system, a solid-phase extraction system, a sample preparation system, a capillary electrophoresis instrument, combinations thereof, components thereof, variations thereof, and/or the like. Although LC, MS, and LC-MS are used in examples in this detailed description, embodiments are not so limited, as other analytical instruments capable of operating according to some embodiments are contemplated herein.

In some embodiments, analytical instrument 115 may operate to perform an analysis. For example, for an LC-MS system, analytical instrument 115 may separate a sample and perform mass analysis on the separated sample to generate analytical information 136. Analytical information 136 may be or may include information associated with properties of sample constituents, such as precursor molecule or ion information, product molecule or ion information, retention time, drift time, charge, mass, m/z, and/or the like. In exemplary embodiments, analytical information 136 may be or may include information generated as the result of an analysis performed by analytical instrument 115, such as values, graphs, images, calculations, signals, and/or the like.

In various embodiments, analysis system 105 may include computing device 110 communicatively coupled to analytical instrument 115 or otherwise configured to receive and store analytical information 136 associated with analytical instrument 115. For example, analytical instrument 115 may operate to provide analytical information to a location on a network 150 accessible to computing device 110, for instance, a cloud computing environment and/or nodes 152a-n. In some embodiments, computing device 110 may be operative to control, monitor, manage, or otherwise process various operational functions of analytical instrument 11. In some embodiments, computing device 110 may be or may include a stand-alone computing device, such as a personal computer (PC), server, tablet computing device, cloud computing device, and/or the like.

As shown in FIG. 1, computing device 110 may include processing circuitry 120, a memory unit 130, and a transceiver 140. Processing circuitry 120 may be communicatively coupled to memory unit 130 and/or transceiver 140.

Processing circuitry 120 may include and/or may access various logic for performing processes according to some embodiments. For instance, processing circuitry 120 may include and/or may access compound encoding logic 122. In general, compound encoding logic 122 can be circuitry arranged to perform specific operations related to processing a distributed ledger, such as, for example, encoding, decoding, encrypting, decrypting, validating, or the like. Processing circuitry and/or compound encoding logic 122, or portions thereof, may be implemented in hardware, software, or a combination thereof. As used in this application, the terms "logic," "component," "layer," "system," "circuitry," "decoder," "encoder," and/or "module" are intended to refer to a computer-related entity, either hardware, a combination of hardware and software, software, or software in execution, examples of which are provided by the exemplary computing architecture 1000. For example, a logic, circuitry, and/or the like may be and/or may include, but are not limited to, a process running on a processor, a processor, a hard disk drive, multiple storage drives (of optical and/or magnetic storage medium), an object, an executable, a thread of execution, a program, a computer, hardware circuitry, integrated circuits, application specific integrated circuits (ASIC), programmable logic devices (PLD), digital signal processors (DSP), field programmable gate array (FPGA), a system-on-a-chip (SoC), memory units, logic gates, registers, semiconductor device, chips, microchips, chip sets, software components, programs, applications, firmware, software modules, computer code, combinations of any of the foregoing, and/or the like.

Although compound encoding logic 122 is depicted in FIG. 1 as being within processing circuitry 120, embodiments are not so limited. For example, compound encoding logic 122 may be located within an accelerator, a processor core, an interface, an individual processor die, implemented entirely as a software application (for instance, compound encoding application 132) and/or the like.

Memory unit 130 may include various types of computer-readable storage media and/or systems in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In addition, memory unit 130 may include various types of computer-readable storage media in the form of one or more lower speed memory units, including an internal (or external) hard disk drive (HDD), a magnetic floppy disk drive (FDD), and an optical disk drive to read from or write to a removable optical disk (e.g., a CD-ROM or DVD), a solid state drive (SSD), and/or the like.

Memory unit 130 may store a compound encoding application 132 that may operate, alone or in combination with compound encoding logic 122, to perform various compound encoding functions according to some embodiments. For example, compound encoding application 132 may generate and/or maintain an encoded molecule library 134 in memory unit 130, a node 152a-n of network 150, a data store, and/or the like. In various embodiments, compound encoding application 132 may process analytical information 136 (alone or in combination with other information to generate encoded representations for encoded molecule library 134.

Figure 2A:
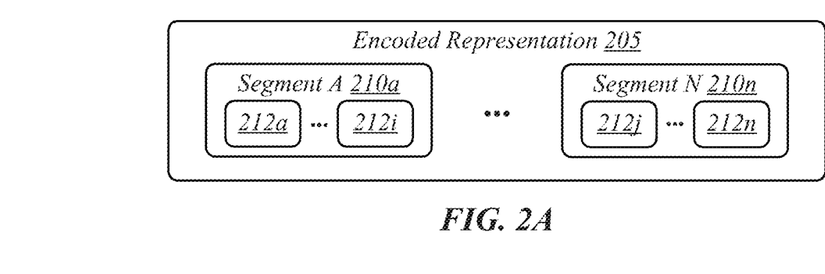
FIGS. 2A and 2B depict illustrative encoded representations according to some embodiments.

Referring now to FIGS. 2A and 2B, therein is depicted encoded representations according to some embodiments. As shown in FIG. 2A, an encoded representation 205 may be formed of at least one segment 210a-n having at least one symbol 212a-n. At least a portion of each segment 210a-n may be used to encode one or more properties of a compound. For example, in some embodiments, a portion of a segment 210a-n may include unspecified or otherwise unused symbols that do not include information used to represent a compound (for instance, leading or trailing 0 s or other symbols). In some embodiments, at least one segment 210a-n and/or a portion thereof may be used to include information for identifying other aspects besides a characteristic of a compound, such as a device identifier, sample identifier, sample type (for instance, toxicology, food and environment, pharmaceutical, biomedical, and/or the like), time stamp information, operator information, experimental information (for instance, duration, heat, humidity, sample preparation information, analysis information (e.g., MS, tandem MS)), facility information, and/or the like.

In some embodiments, at least one segment 210a-n and/or portion thereof may include a primary key, for example, a separate encoding relating to samples, data identifiers (for instance, spectrum IDs) used in the generation of encoded representation 205 and/or a portion thereof (for instance, segments 210a-n, symbols 212a-n, and/or the like). In various embodiments, the primary key may provide for, among other things, keeping a chain of custody between analytical information 136 (for instance, spectrum metadata) and corresponding encoded representation(s) 205.

For instance, an encoded representation 205 may include a header or other segment 210a-n that includes metadata associated with the sample, compound, confidence indicator, library indicator, and/or other aspect associated with the encoded representation.

Figure 2B:
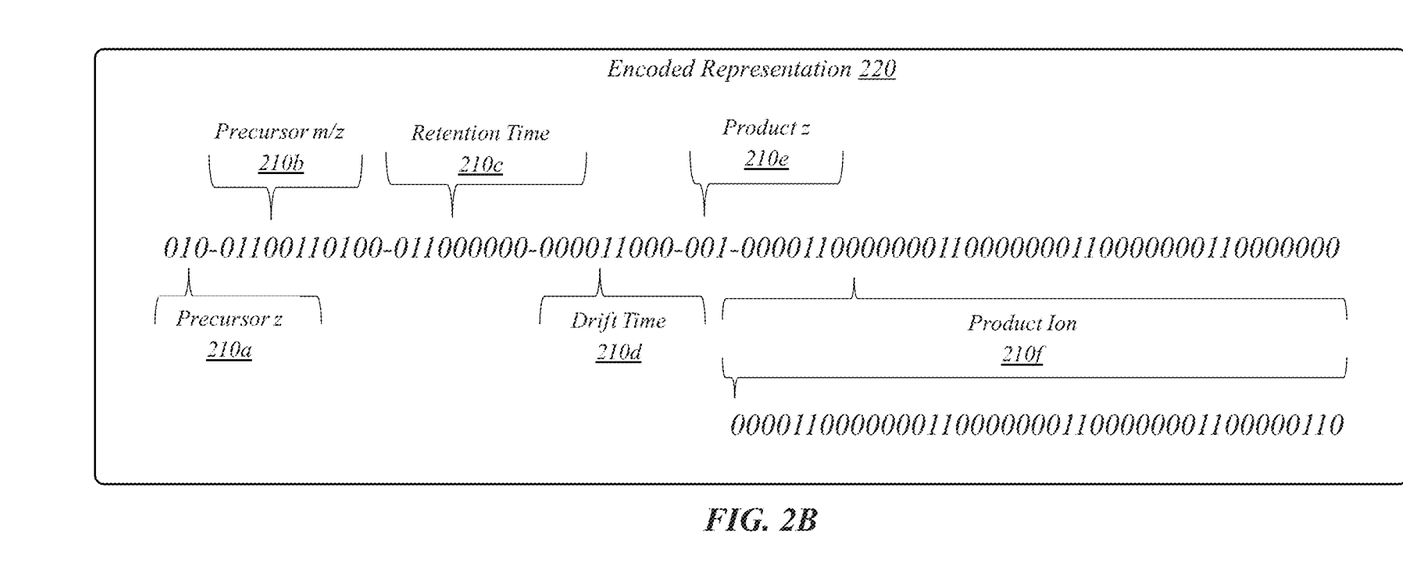

As shown in FIG. 2B, an encoded representation 220 may be used to encode specific information about a compound using segments 210a-f having binary symbols. In some embodiments, the particular encoded representation 220 of FIG. 2B may be referred to as a High-Entropy Digital Molecular Ion Signature (HE-DMIS or DMIS). For instance, encoded representation 220 may include a precursor z segment 210a, a precursor m/z segment 210b, a retention time segment 210c, a drift time segment 210d, a product z segment, and/or a product ion 210f segment. In some embodiments, one or more symbols 212a-n may be used to signify a characteristic of a segment 210a-n, such as the relevance of the data for the sample, analysis, compound, and/or the like. For example, if the first symbol of the drift time segment 210d is a "1," this may signify that this information is not relevant for the sample (or vice versa).

An encoded representation 220 may include more less segments as encoded representation 220 is for illustrative purposes. In some embodiments, an encoded representation may include 1 segment, 2 segments, 3 segments, 5 segments, 10 segments, 20 segments, 50 segments, 100 segments, 1000 segments, and any value or range between any of these values (including endpoints). In various embodiments, an encoded representation 205 may include any type of segment that may be used to identify a compound and/or compounds related thereto, including m, z, m/z, precursor z, precursor m/z, product z, product ion, retention time, drift time, and/or the like. In exemplary embodiments, an encoded representation may include any type of character that may be used to encode information, including, without limitation, alphanumeric characters, binary symbols, and/or the like. In various embodiments, encoded representation may include 128 bits. In some embodiments, encoded representation 205 may include 8 bits, 16 bits, 32 bits, 64 bits, 128 bits, 256 bits, 512 bits, 1 KB, 1 MB, 1 TB, and any value or range between any two of these values. Embodiments are not limited in this context.

In the encoded representation 220 of FIG. 2B, precursor and/or product z may be represented by $2^3$ bits, precursor m/z may be represented by $2^{11}$ bits, time (retention and/or drift (for instance, IMS drift time)) may be represented by $2^{10}$ bits. In various embodiments, encoded representation 205 may provide precursor encoding of 3+11+10+10=34 bits.

In various embodiments, data or metadata including, z, m/z, relative retention time, relative drift time (for instance, for IMS), and/or collisional cross-sectional area (CCS A2) for every precursor ion and its associated product ions, may be encoded into a HE-DMIS, such as a 128-bit HE-DMIS. In some embodiments, 34 of the 128 bits may be used for encoding the precursor ion metadata with the remaining 94-bits reserved for the product ion metadata.

For example, encoded representation 220 may depict the encoding of a 3-dimensional product ion spectrum, including an m/z dimension, a retention time dimension, and a drift time dimension. In a 3-dimensional experiment, the encoding may include, for precursor ions, z (3-bits), integer m/z (11-bits), normalized retention-time (10-bits), normalized drift-time (10-bits). For product ions, z (3-bit) and product ion m/z (91-bits) may be encoded. In various embodiments, for 2-dimensional data (for instance, that does not include chromatographic or ion mobility separation), the 10-bits used for encoding the normalized value may be added to the product ion encoding.

Experimentally generated HE-DMIS s from a plurality of samples may be initially matched by their precursor ion encoding. The product ion encodings of the matched precursors, including product ion z, may then be correlated. For instance, only those bits illustrating a statistically significant match rate ($p<0.01$) may be retained for creating a putative or potential DMIS. In some embodiments, potential DMISs from multiple ensembles may be matched and correlated until no matter how many more data sets are added the matched bins never change. It is at this point that the potential DMIS may become or become designated as a HE-DMIS, for example, and added to an encoded molecule library 134 as a target for automated high-throughput screening according to some embodiments. In various embodiments, each HE-DMIS may include a primary key, for instance, a separate encoding relating to all samples and spectrum ID used in its creation. The primary key may provide for, among other things, keeping a chain of custody between the spectrum or other metadata and its HE-DMIS.

Figure 3:
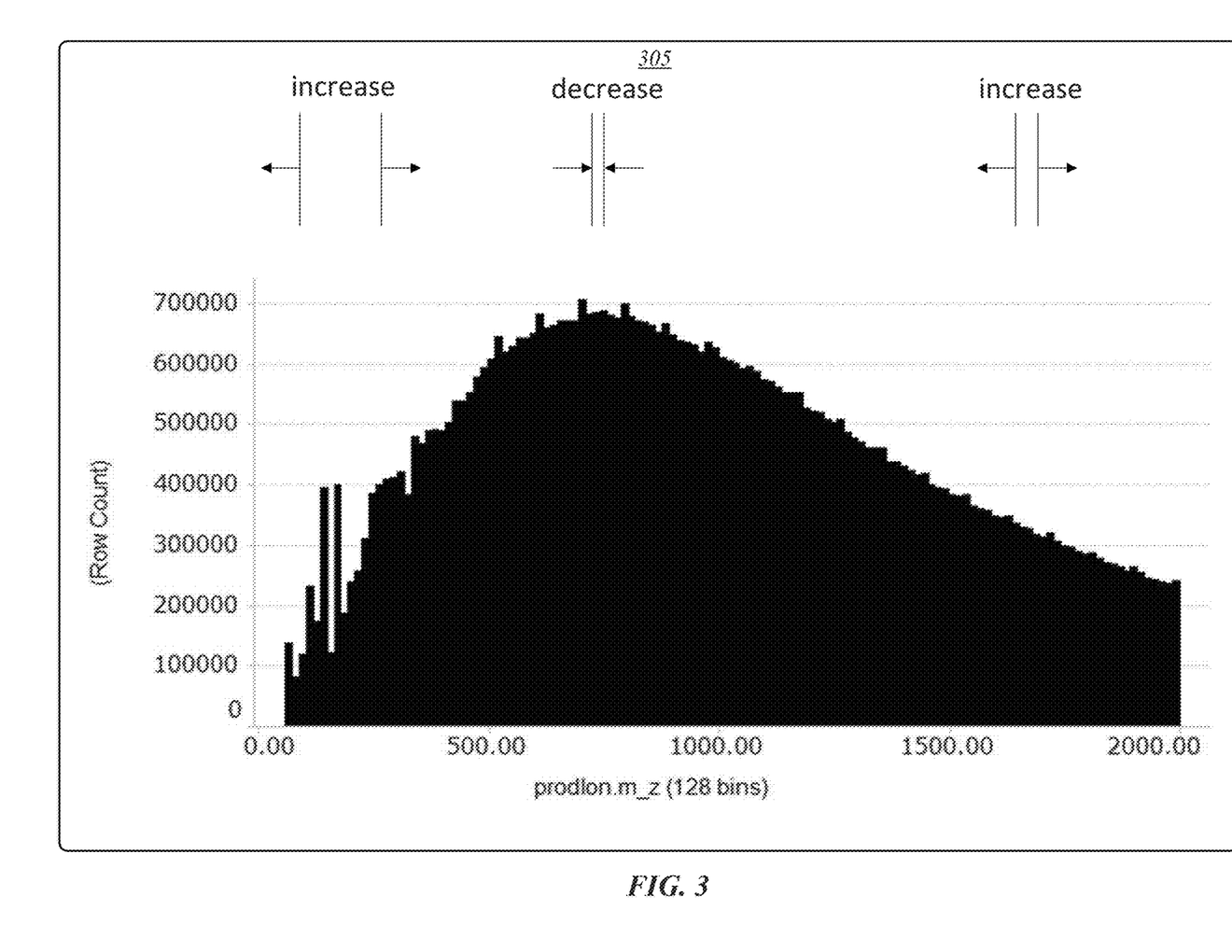
FIG. 3 illustrates a natural distribution of product ion m/z values according to some embodiments.

FIG. 3 illustrates a natural distribution of product ion m/z values. For example, FIG. 3 depicts a graph 305 of the natural distribution of product ion m/z values generated via in-silico tryptic digestion of 7,500 randomly selected human proteins (for instance, trypsin). The illustrated distribution could have been generated from in-silico product ions generation from any class of chemical compounds including but not limited to lipids, metabolites and other natural products, food, pesticides, cosmetics and other chemical materials like hydro carbons and polyethylene glycols. The distribution of the in-silico product ion m/z values can be filtered by both precursor and product ion z. In some embodiments, a product ion bin width (m/z) for each bit may be varied based on these distributions. For example, in some embodiments, an encoding process may set each bit's bin width such that the number of possible product ions per bin is similar or substantially similar (for instance, as near as possible to being the same). Limiting the maximum m/z by z and varying each bit's bin width by the natural distribution of integer m/z, z increases the entropy of the DMIS relative to a simple division of a fixed m/z sale by the number of available bits.

In various embodiments, normalization of retention time and/or drift time may include DMISs across the ensemble of datasets being correlated and the match rate for each calculated. If the match rate of the precursor ion and product ion encodings relative to the total number of datasets in the ensemble is deemed statistically significant (for instance, p<0.01) a composite DMSI may be created retaining only the matched product ion bits that with a match rate that was deemed statistically significant. For DMISs of identified compounds (for instance, peptides from database searches), a normalized intensity may be calculated for each matched product ion. For example, in various embodiments, a normalized intensity may be or may include the intensity ratio of each individual matched product ion's intensity to the sum of the total. In DMISs with a disproportionate number of validated bits (for example, greater than 7) the normalized intensity plays a role in limiting which bits are to be used. There may be a minimum and maximum number of bits required for HE-DMIS. The maximum and minimum values may be predicated on the precursor ion integer m/z and/or z as well as the product ions z, and which bits across the mass scale are active. When examining a corresponding histogram (for instance, count verses bit) by integer precursor m/z and z, some bits may be matched at a much higher frequency than others. Accordingly, in exemplary embodiments, by selecting high replicating lower frequency bits for the DMIS entropy may be increased.

Figure 4:
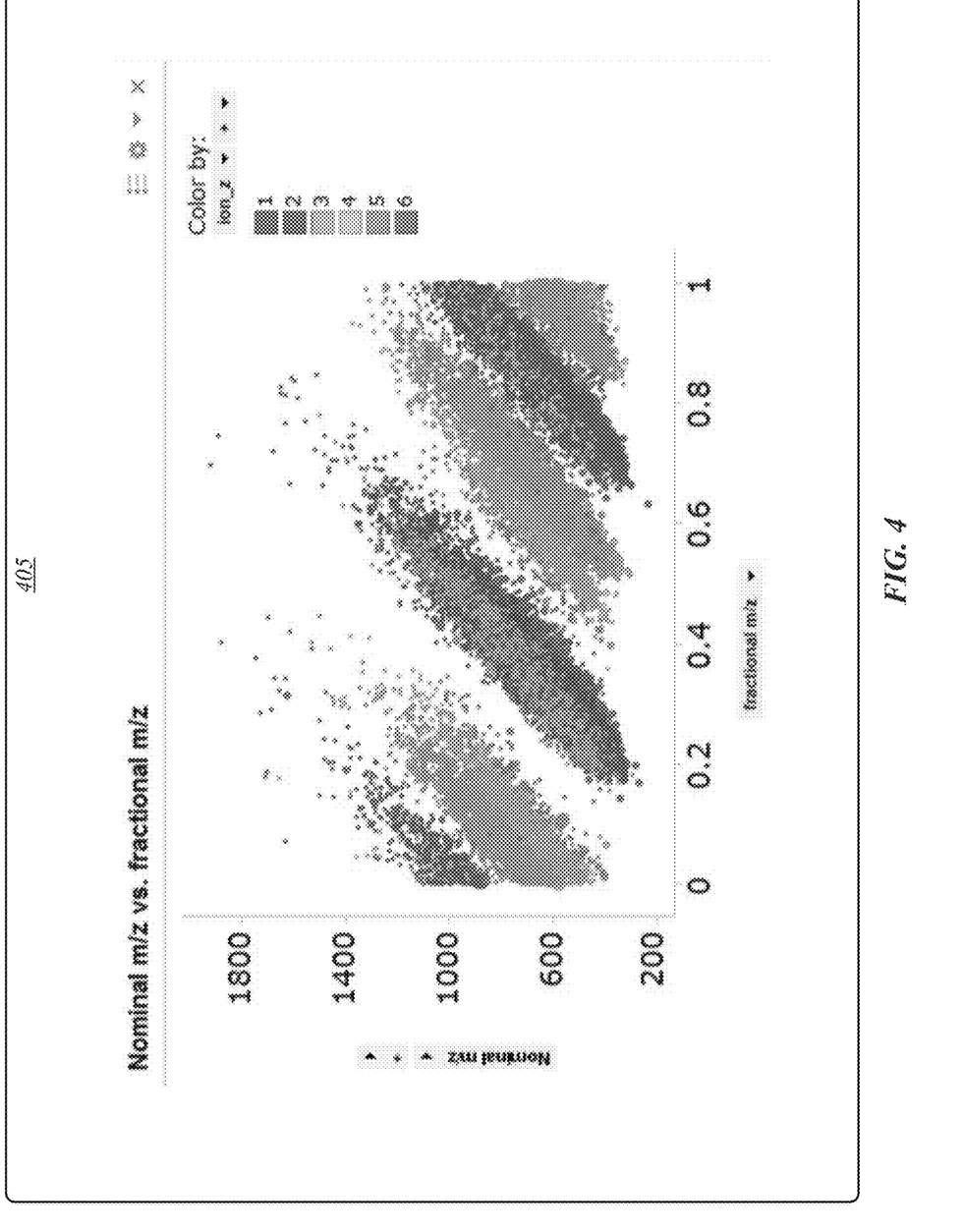
FIG. 4 depicts a graph of mass defect versus integer m/z value of product ions according to some embodiments.

FIG. 4 depicts mass defect (fractional m/z) versus the integer m/z value of the product ions. As shown in FIG. 4, a scatter plot 405 includes an x-axis representing a fractional part (mass defect) of the molecular ion and the y-axis represents the integer value. A non-limiting description of the relationship between a molecular ion's charge and its integer and fraction m/z, as well as if IMS employed, drift time is included in U.S. Pat. No. 9,734,996, incorporated by reference herein. The data bands of scatter plot 405 may represents the charge-state of the product ion m/z. The distribution may be the same for precursor ions.

Figure 5:
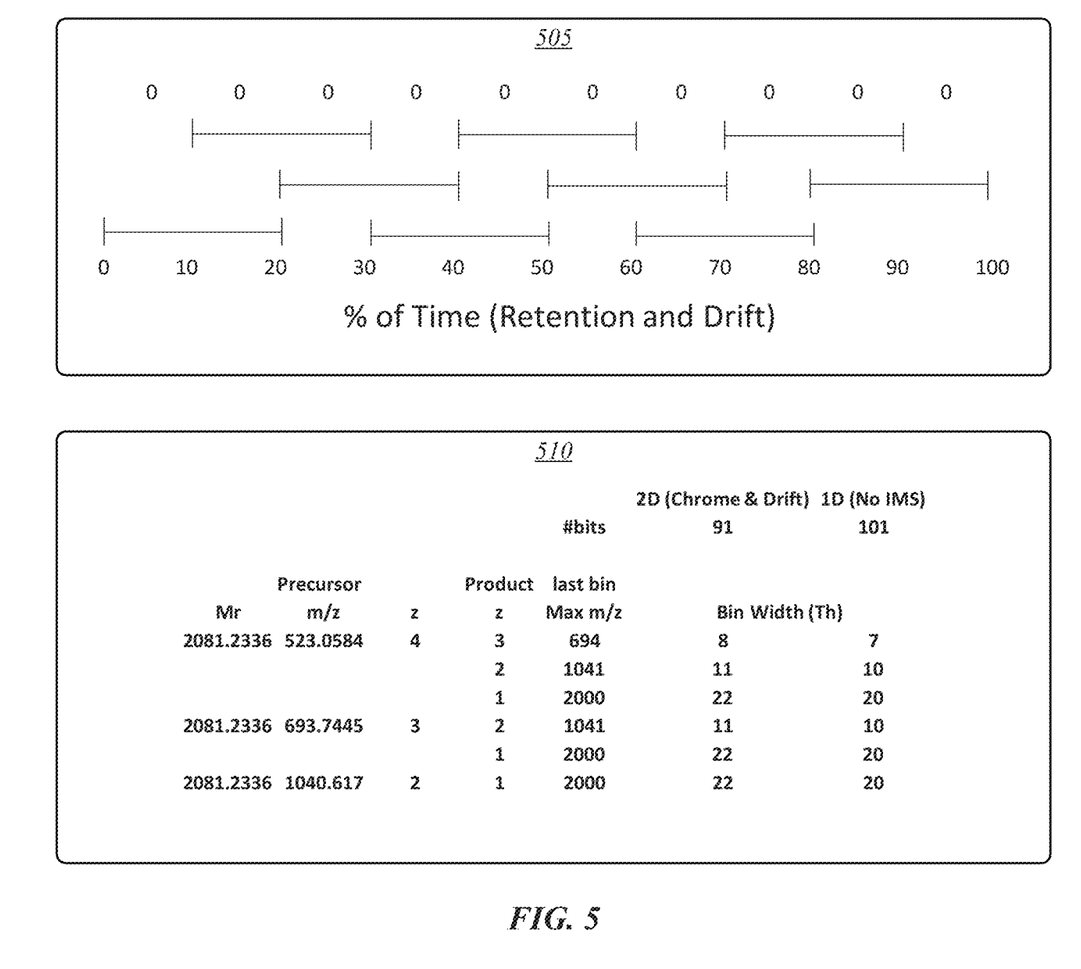
FIG. 5 depicts information associated with a percentage of time for retention time and drift time according to some embodiments.

FIG. 5 depicts a representation 510 of percentage of time for retention time and drift time and a table 510 of DMIS s exceeding a minimum number of matched product ion bits sorted by match rate descending and retention time ascending. Time zero is assigned to the highest match rate earliest eluting encoded precursor with 100 being assigned to the last. The absolute time difference is measured, and each individual time normalized to the difference, converting time to a % of time. Given that hydrophobicity is an immutable property of a chemical compound, elution order should be maintained providing a similar buffer system and column matrix.

In some embodiments, precursor and/or product ion spectra may be created according various methods. Knowing each precursor ions' m/z allows the encoding process to set the maximum m/z value for the last m/z bin in the product ion encoding. In some embodiments, the width in m/z for each bin can be set by dividing the maximum m/z by the number of bits used in the product ion encoding. The number of HE-DMISs generated per-precursor may be a direct function of its charge-state. For example, when the mechanism of fragmentation is a collision cell, the maximum charge-state of a product ions is limited to the precursor ion's charge minus one for charge-states greater than one. Singly charged ions when fragmented produce product ions of the same charge-state. As such, 1+ and 2+ precursor ions when fragmented in a collision cell produced singly charged product ions. Precursor ions of a charge-state greater than two can produced product ions from 1+ to the precursor ions' z minus one.

For certain mass analyzers, there may be a maximum measurable m/z value that can be either isolated and or transmitted. Accordingly, there may be a highest product ion m/z value that can be encoded to a precursor ion of a given m/z and z. Table 510 of FIG. 5 illustrates how the product ion encoding may be done by both precursor $M_r$ and product ion m/z and z. In some embodiments, they may be associated to a corresponding set of product ions. In various embodiments, the maximum charge state of a production generated via collisional disassociation (collision cell) may be equal to the precursor ion's charge-state minus 1. In exemplary embodiments, maximum product ion m/z for encoding may be directly related to the number of bits used for product ion encoding, which may vary by the number of experimentally available pre-ion detection separation techniques (for example, chromatographic, ion mobility, and/or the like) employed. For example, single dimension separations may require only 10-bits while 2-dimensional separations may require 20. Embodiments are not limited in this context.

Generation of HE-DMIS library data as detailed herein may subsequently be used in high throughput screening applications using lower-resolution instrumentation. For example, HE-DMIS library data may be compared against such experimentally-derived data through consideration of the relative detection differences between the HE-DMIS library data and the experimentally derived data (e.g., sensitivity, resolution, dynamic range). For example, HE-DMIS data may be generated using high-resolution MS of molecular ions in simple and complex mixtures. These HE-DMIS may then be used as targets to identify and quantify these molecular ions and their surrogates in low-resolution instrumentation.

In conventional systems, MS data may be searched using known libraries (i.e., NIST, METLIN, etc.) after the MS data has been generated and processed by the MS system. Conventional systems require large amount of MS data to facilitate ion processing (for instance, ion identification and/or quantification), typically on the order of terabytes of data. However, HE-DMIS data may replace the large volume of MS data in a compact form without sacrificing ion processing accuracy. Accordingly, HE-DMIS data may allow for real-time ion processing at the site of data generation (for instance, at the analytical instrument). For instance, because an operator may already have the HE-DMIS data, if the operator seeks to detect pesticides, for example, the operator may pull HE-DMIS data down from the cloud (or other remote storage system) very small amounts of information that could be used at the point of acquisition as MS data are being generated in the instrument. Accordingly, in some embodiments, HE-DMIS data may be used as filters to perform real-time identification of the ions that are being detected in the instrument. In this manner, the need to store or use all of the MS data is reduced or even eliminated through the use of HE-DMIS data, in particular, all that is required are one or more strings of symbols or bits of an HE-DMIS representation.

Figure 6:
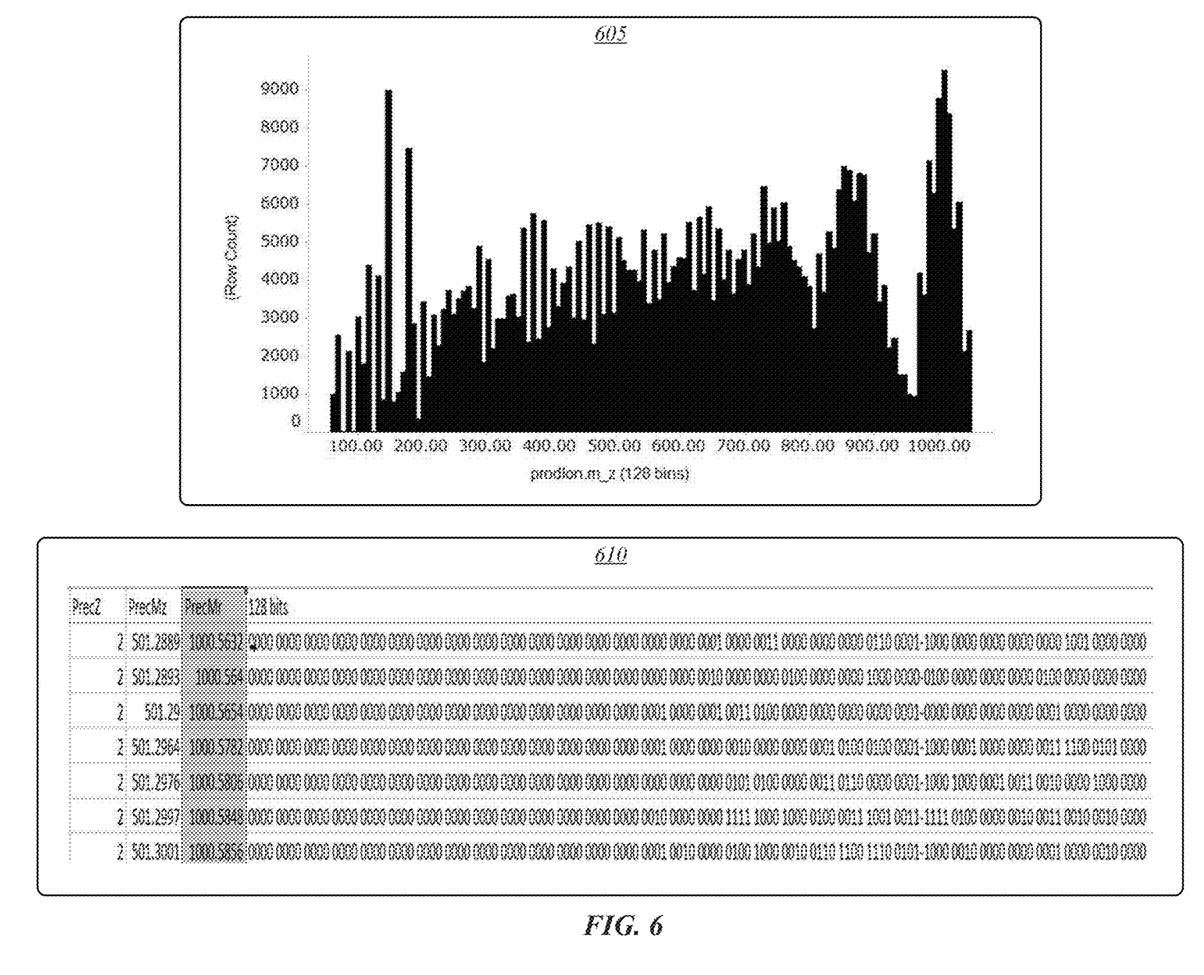
FIG. 6 depicts an illustrative graph and table for generating bin vectors.
Figure 7:
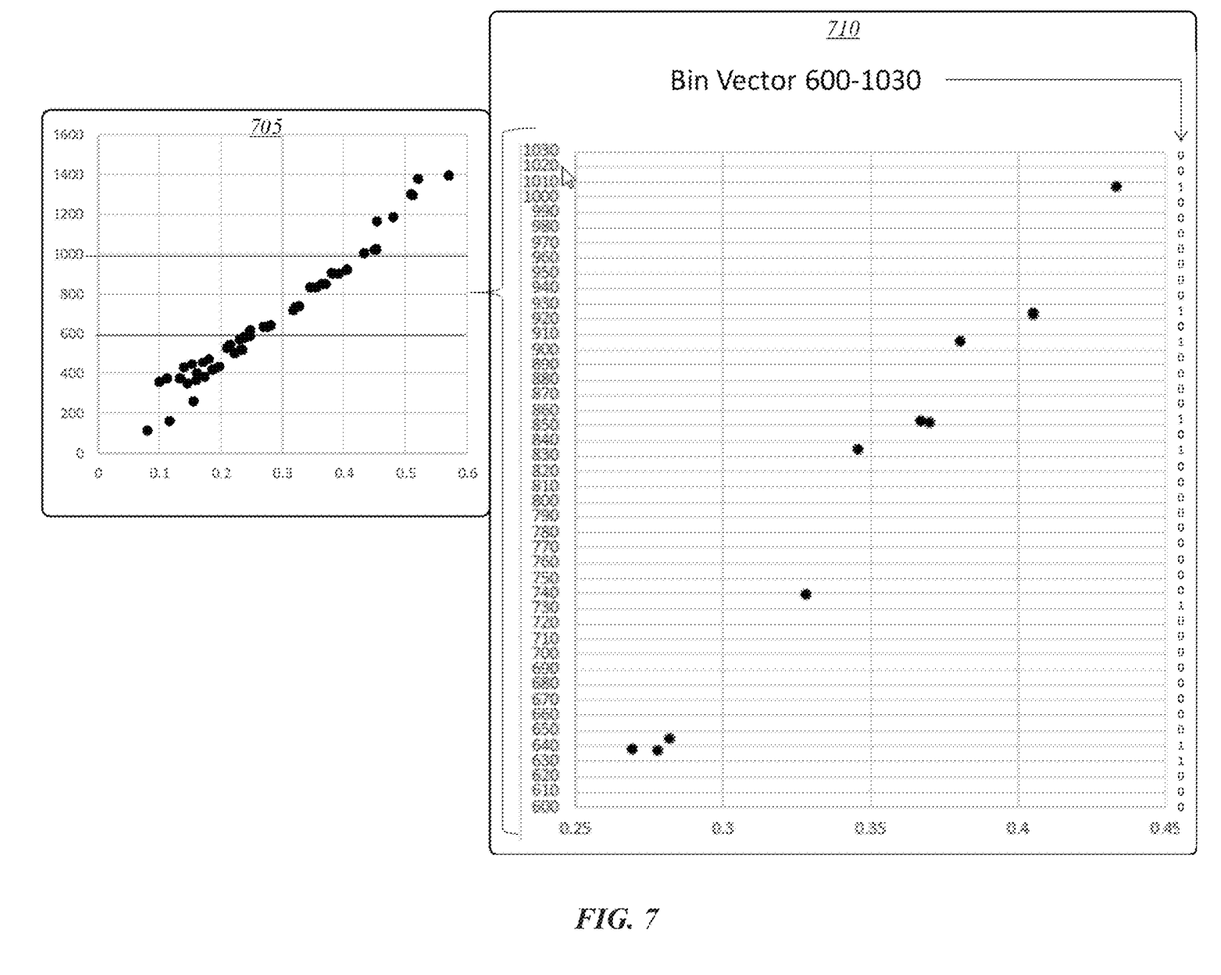
FIG. 7 depicts a graph of m/z versus mass defect for a set of ions and a table of a corresponding bin vector.
Figure 8:
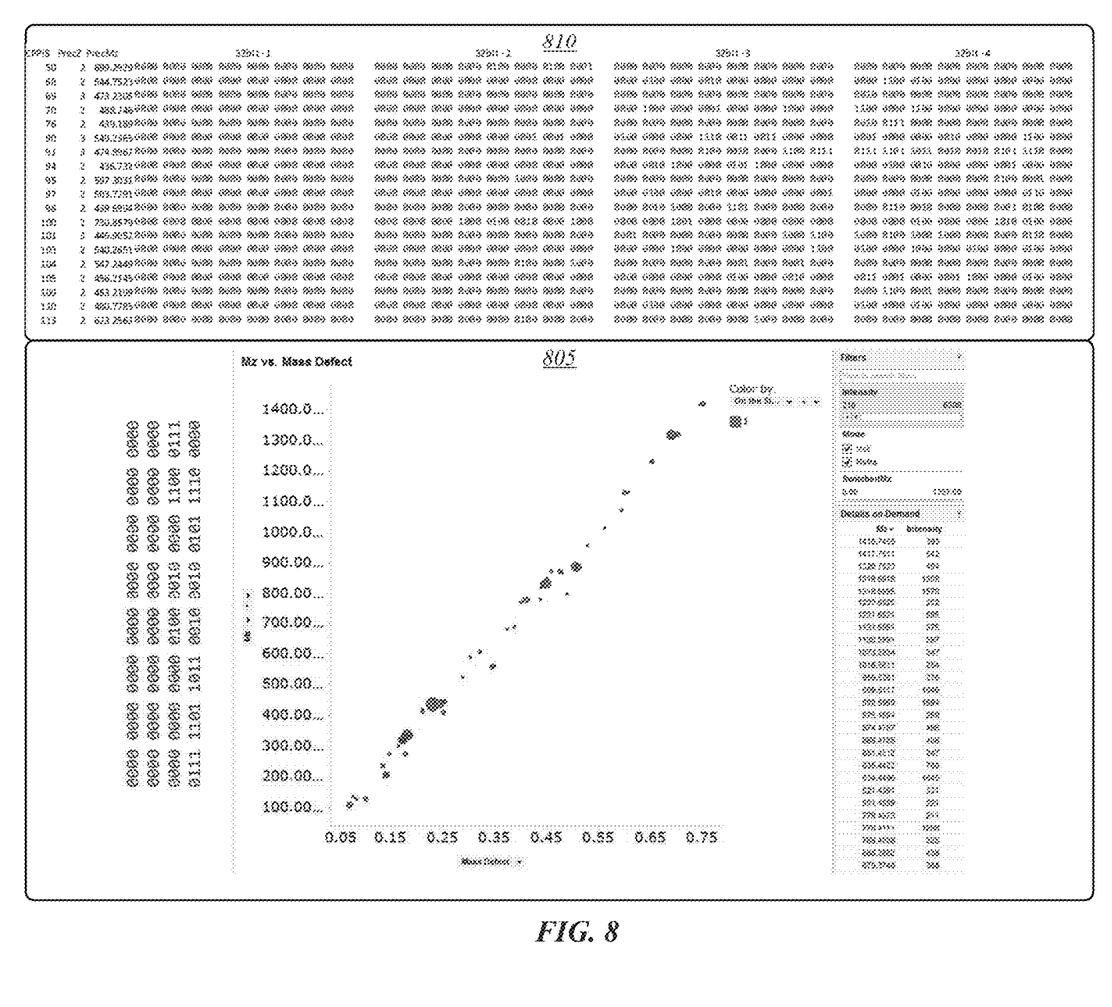
FIG. 8 depicts a graph of m/z versus mass defect for a set of ions and a table of a corresponding bin vector.
Figure 9:
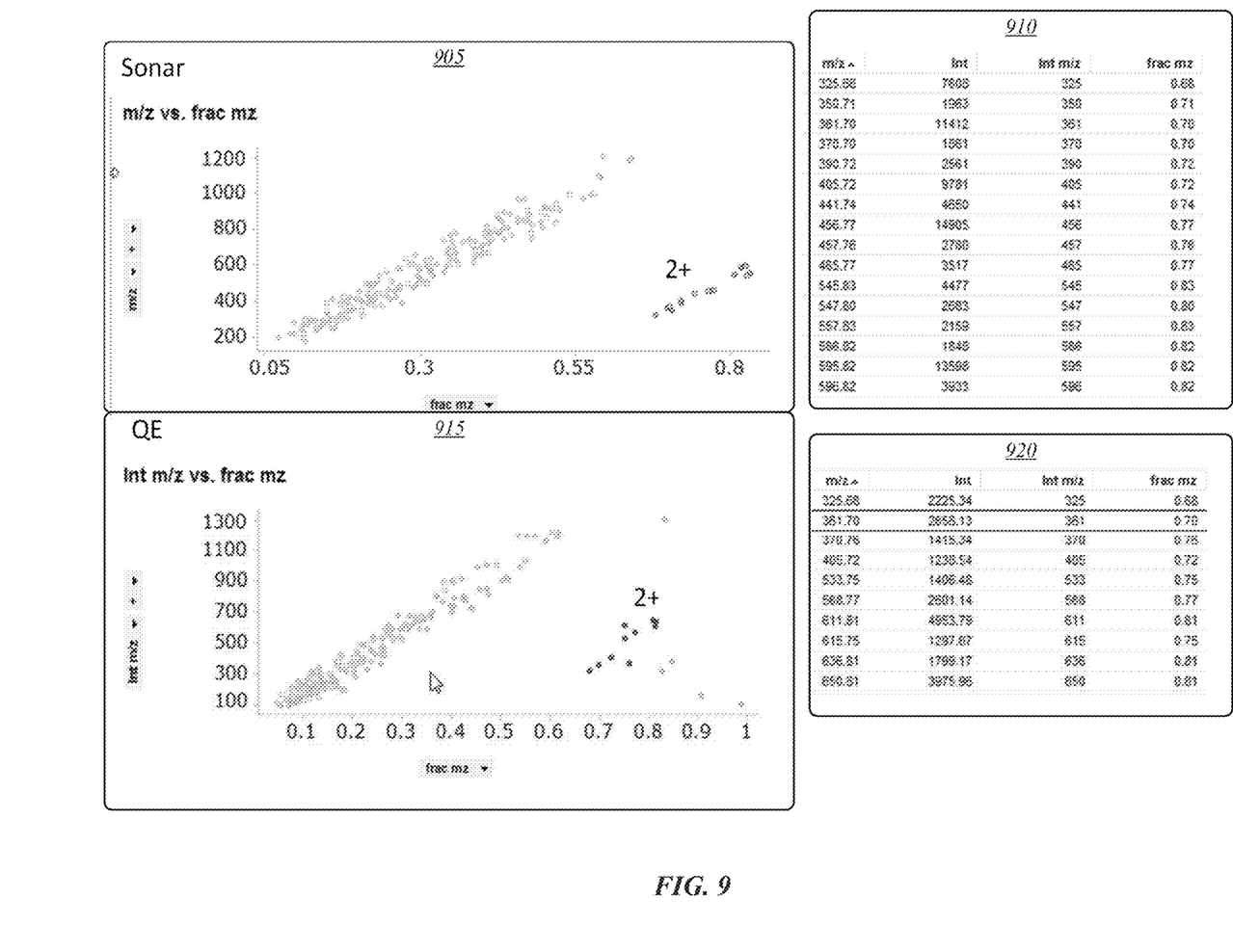
FIG. 9 depicts graphs for m/z versus fractional m/z and corresponding data tables

FIG. 6 depicts an illustrative graph 605 and table 610 for generating bin vectors. In some embodiments, a bin vector may include a string of symbols corresponding to m/z values. In various embodiments, a bin vector symbol may have a value of 1 if an ion is determined at that m/z value and a value of 0 otherwise. For example, once the product ion m/z bins have been normalized (for instance, for precursors of $M_r$ 1000 to 1050), the calculated bin widths may be used to generate bin vectors (for instance, 128 bin vectors) for various spectra or other analytical data. In some embodiments, the spectra may include simulated spectra, validated spectra, and/or experimental composite product ion spectra. FIG. 7 depicts a graph 705 of m/z versus mass defect for a set of ions and a table 710 of a corresponding bin vector for the range of 600-1030 m/z. FIG. 8 depicts a graph 805 of m/z versus mass defect for a set of ions and a table 810 of a corresponding bin vector. FIG. 9 depicts graph 905 for m/z versus fractional m/z for a Sonar analysis and corresponding data table 910, and graph 915 for m/z versus fractional m/z for a QE analysis and corresponding data table 920.

Figure 10:
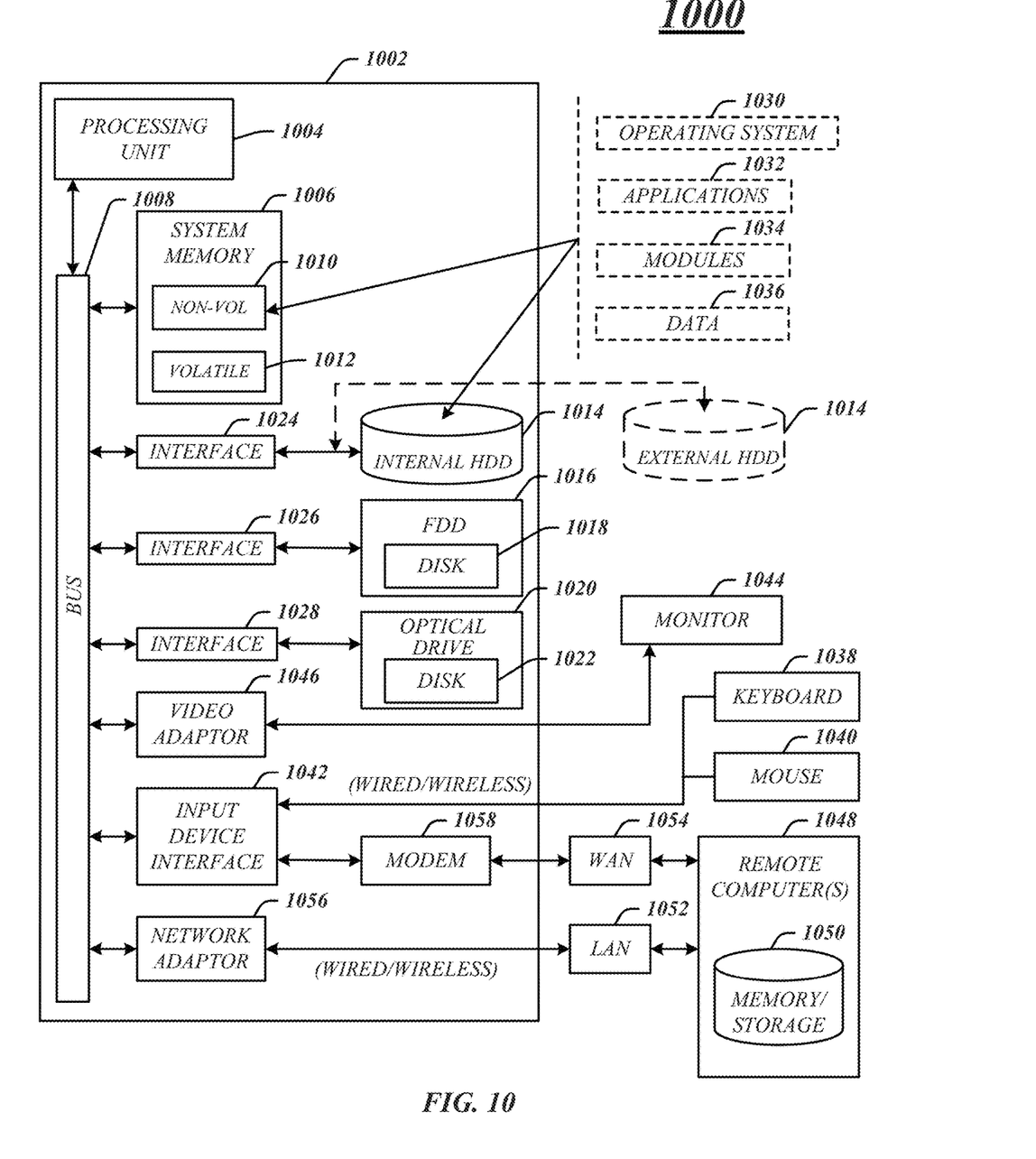
FIG. 10 illustrates an embodiment of a computing architecture.

FIG. 10 illustrates an embodiment of an exemplary computing architecture 1000 suitable for implementing various embodiments as previously described. In various embodiments, the computing architecture 1000 may comprise or be implemented as part of an electronic device. In some embodiments, the computing architecture 1000 may be representative, for example, of computing device 110. Embodiments are not limited in this context.

As used in this application, the terms "system" and "component" and "module" are intended to refer to a computer-related entity, either hardware, a combination of hardware and software, software, or software in execution, examples of which are provided by the exemplary computing architecture 1000. For example, a component can be, but is not limited to being, a process running on a processor, a processor, a hard disk drive, multiple storage drives (of optical and/or magnetic storage medium), an object, an executable, a thread of execution, a program, and/or a computer. By way of illustration, both an application running on a server and the server can be a component. One or more components can reside within a process and/or thread of execution, and a component can be localized on one computer and/or distributed between two or more computers. Further, components may be communicatively coupled to each other by various types of communications media to coordinate operations. The coordination may involve the uni-directional or bi-directional exchange of information. For instance, the components may communicate information in the form of signals communicated over the communications media. The information can be implemented as signals allocated to various signal lines. In such allocations, each message is a signal. Further embodiments, however, may alternatively employ data messages. Such data messages may be sent across various connections. Exemplary connections include parallel interfaces, serial interfaces, and bus interfaces.

The computing architecture 1000 includes various common computing elements, such as one or more processors, multi-core processors, co-processors, memory units, chipsets, controllers, peripherals, interfaces, oscillators, timing devices, video cards, audio cards, multimedia input/output (I/O) components, power supplies, and so forth. The embodiments, however, are not limited to implementation by the computing architecture 1000.

As shown in FIG. 10, the computing architecture 1000 comprises a processing unit 1004, a system memory 1006 and a system bus 10010. The processing unit 1004 can be any of various commercially available processors, including without limitation an AMD® Athlon®, Duron® and Opteron® processors; ARM® application, embedded and secure processors; IBM® and Motorola® DragonBall® and PowerPC® processors; IBM and Sony® Cell processors; Intel® Celeron®, Core (2) Duo®, Itanium®, Pentium®, Xeon®, and XScale® processors; and similar processors. Dual microprocessors, multi-core processors, and other multi-processor architectures may also be employed as the processing unit 1004.

The system bus 10010 provides an interface for system components including, but not limited to, the system memory 1006 to the processing unit 1004. The system bus 10010 can be any of several types of bus structure that may further interconnect to a memory bus (with or without a memory controller), a peripheral bus, and a local bus using any of a variety of commercially available bus architectures. Interface adapters may connect to the system bus 10010 via a slot architecture. Example slot architectures may include without limitation Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and the like.

The system memory 1006 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In the illustrated embodiment shown in FIG. 10, the system memory 1006 can include non-volatile memory 1010 and/or volatile memory 1012. A basic input/output system (BIOS) can be stored in the non-volatile memory 1010.

The computer 1002 may include various types of computer-readable storage media in the form of one or more lower speed memory units, including an internal (or external) hard disk drive (HDD) 1014, a magnetic floppy disk drive (FDD) 1016 to read from or write to a removable magnetic disk 10110, and an optical disk drive 1020 to read from or write to a removable optical disk 1022 (e.g., a CD-ROM or DVD). The HDD 1014, FDD 1016 and optical disk drive 1020 can be connected to the system bus 10010 by a HDD interface 1024, an FDD interface 1026 and an optical drive interface 10210, respectively. The HDD interface 1024 for external drive implementations can include at least one or both of Universal Serial Bus (USB) and IEEE 13104 interface technologies.

The drives and associated computer-readable media provide volatile and/or nonvolatile storage of data, data structures, computer-executable instructions, and so forth. For example, a number of program modules can be stored in the drives and memory units 1010, 1012, including an operating system 1030, one or more application programs 1032, other program modules 1034, and program data 1036. In one embodiment, the one or more application programs 1032, other program modules 1034, and program data 1036 can include, for example, the various applications and/or components of apparatus 105, 205, 305, and/or 405.

A user can enter commands and information into the computer 1002 through one or more wire/wireless input devices, for example, a keyboard 10310 and a pointing device, such as a mouse 1040. Other input devices may include microphones, infra-red (IR) remote controls, radio-frequency (RF) remote controls, game pads, stylus pens, card readers, dongles, finger print readers, gloves, graphics tablets, joysticks, keyboards, retina readers, touch screens (e.g., capacitive, resistive, etc.), trackballs, trackpads, sensors, styluses, and the like. These and other input devices are often connected to the processing unit 1004 through an input device interface 1042 that is coupled to the system bus 1010, but can be connected by other interfaces such as a parallel port, IEEE 13104 serial port, a game port, a USB port, an IR interface, and so forth.

A monitor 1044 or other type of display device is also connected to the system bus 10010 via an interface, such as a video adaptor 1046. The monitor 1044 may be internal or external to the computer 802. In addition to the monitor 1044, a computer typically includes other peripheral output devices, such as speakers, printers, and so forth.

The computer 1002 may operate in a networked environment using logical connections via wire and/or wireless communications to one or more remote computers, such as a remote computer 10410. The remote computer 10410 can be a workstation, a server computer, a router, a personal computer, portable computer, microprocessor-based entertainment appliance, a peer device or other common network node, and typically includes many or all of the elements described relative to the computer 1002, although, for purposes of brevity, only a memory/storage device 1050 is illustrated. The logical connections depicted include wire/wireless connectivity to a local area network (LAN) 1052 and/or larger networks, for example, a wide area network (WAN) 1054. Such LAN and WAN networking environments are commonplace in offices and companies, and facilitate enterprise-wide computer networks, such as intranets, all of which may connect to a global communications network, for example, the Internet.

When used in a LAN networking environment, the computer 1002 is connected to the LAN 1052 through a wire and/or wireless communication network interface or adaptor 1056. The adaptor 1056 can facilitate wire and/or wireless communications to the LAN 1052, which may also include a wireless access point disposed thereon for communicating with the wireless functionality of the adaptor 1056.

When used in a WAN networking environment, the computer 1002 can include a modem 10510, or is connected to a communications server on the WAN 1054, or has other means for establishing communications over the WAN 1054, such as by way of the Internet. The modem 10510, which can be internal or external and a wire and/or wireless device, connects to the system bus 10010 via the input device interface 1042. In a networked environment, program modules depicted relative to the computer 1002, or portions thereof, can be stored in the remote memory/storage device 1050. It will be appreciated that the network connections shown are exemplary and other means of establishing a communications link between the computers can be used.

The computer 1002 is operable to communicate with wire and wireless devices or entities using the IEEE 802 family of standards, such as wireless devices operatively disposed in wireless communication (e.g., IEEE 802.16 over-the-air modulation techniques). This includes at least Wi-Fi (or Wireless Fidelity), WiMax, and Bluetooth™ wireless technologies, among others. Thus, the communication can be a predefined structure as with a conventional network or simply an ad hoc communication between at least two devices. Wi-Fi networks use radio technologies called IEEE 802.11x (a, b, g, n, etc.) to provide secure, reliable, fast wireless connectivity. A Wi-Fi network can be used to connect computers to each other, to the Internet, and to wire networks (which use IEEE 802.3-related media and functions).

Numerous specific details have been set forth herein to provide a thorough understanding of the embodiments. It will be understood by those skilled in the art, however, that the embodiments may be practiced without these specific details. In other instances, well-known operations, components, and circuits have not been described in detail so as not to obscure the embodiments. It can be appreciated that the specific structural and functional details disclosed herein may be representative and do not necessarily limit the scope of the embodiments.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

Unless specifically stated otherwise, it may be appreciated that terms such as "processing," "computing," "calculating," "determining," or the like, refer to the action and/or processes of a computer or computing system, or similar electronic computing device, that manipulates and/or transforms data represented as physical quantities (e.g., electronic) within the computing system's registers and/or memories into other data similarly represented as physical quantities within the computing system's memories, registers or other such information storage, transmission or display devices. The embodiments are not limited in this context.

It should be noted that the methods described herein do not have to be executed in the order described, or in any particular order. Moreover, various activities described with respect to the methods identified herein can be executed in serial or parallel fashion.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

The invention claimed is:

1. An apparatus, comprising:
   at least one memory; and
   logic coupled to the at least one memory, the logic to:
      receive analytical information associated with at least one compound,
      generate at least one encoded representation of the at least one compound, the encoded representation comprising at least one segment encoding at least one property of the at least one compound using a plurality of symbols, wherein the at least one property comprises one or more of a charge, a mass, an intensity value for a mass-to-charge ratio, an intensity value for a retention time, an intensity value for a drift time, or collision cross-section data, the generating comprising:

accessing a plurality of ion signatures, each ion signature comprising a plurality of bits representing a precursor ion encoding and a plurality of bits representing a product ion encoding, matching a subset of the plurality of ion signatures based on their respective precursor ion encodings to generate an initial match set, correlating the ion signatures of the initial match set based on their respective product ion encodings, retaining, from among the correlated ion signatures, bits illustrating a match rate of a predetermined statistical significance, the at least one encoded representation comprising the retained bits, and adding the at least one encoded representation to an encoded molecule library configured to provide automated high-throughput screening by providing the at least one encoded representation as a target to identify or quantify molecular species in a sample.

2. The apparatus of claim 1, the analytical information generated during mass analysis of a sample via at least one analytical instrument, the at least one analytical instrument comprising at least one of a liquid chromatography (LC) system, a gas chromatography (GC) system, a mass analyzer system, a mass spectrometer (MS) system, an ion mobility spectrometer (IMS) system, a high-performance liquid chromatography (HPLC) system, a ultra-performance liquid chromatography (UPLC®) system, a ultra-high performance liquid chromatography (UHPLC) system.

3. The apparatus of claim 1, the plurality of symbols comprising binary symbols.

4. The apparatus of claim 1, the at least one compound comprising a product ion and the at least one property comprising a precursor charge or an intensity value for a precursor mass-to-charge ratio.

5. The apparatus of claim 1, the at least one encoded representation comprising a 128-bit string.

6. The apparatus of claim 1, the at least one encoded representation comprising a primary key configured to relate a plurality of samples to the encoded representation and analytical information comprising at least one of analysis information or operating information.

7. The apparatus of claim 1, the at least one segment comprising a plurality of segments, wherein at least one first segment encodes information associated with a precursor ion of the compound and at least one second segment encodes information associated with a product ion of the compound.

8. The apparatus of claim 1, the at least one segment comprising at least one of a charge associated with the at least one compound in a three-bit segment, a relative time associated with the at least one compound in a ten-bit segment, or an intensity value for a mass-to-charge ratio associated with the compound in an eleven-bit segment.

9. The apparatus of claim 1, the logic to:

receive second analytical information associated with a sample, and determine at least one ion present in the sample via a comparison of the second analytical information and the at least one encoded representation.

10. A computer-implemented method, comprising, by a processor:

receiving analytical information associated with at least one compound, generating at least one encoded representation of the at least one compound, the encoded representation comprising at least one segment encoding at least one property of the at least one compound using a plurality of symbols, wherein the at least one property comprises one or more of a charge, a mass, an intensity value for a mass-to-charge ratio, an intensity value for a retention time, an intensity value for a drift time, or collision cross-section data, the generating comprising:

accessing a plurality of ion signatures, each ion signature comprising a plurality of bits representing a precursor ion encoding and a plurality of bits representing a product ion encoding, matching a subset of the plurality of ion signatures based on their respective precursor ion encodings to generate an initial match set, correlating the ion signatures of the initial match set based on their respective product ion encodings, retaining, from among the correlated ion signatures, bits illustrating a match rate of a predetermined statistical significance, the at least one encoded representation comprising the retained bits, and adding the at least one encoded representation to an encoded molecule library configured to provide automated high-throughput screening by providing the at least one encoded representation as a target to identify or quantify molecular species in a sample.

11. The computer-implemented method of claim 10, the analytical information generated during mass analysis of a sample via at least one analytical instrument, the at least one analytical instrument comprising at least one of a liquid chromatography (LC) system, a gas chromatography (GC) system, a mass analyzer system, a mass spectrometer (MS) system, an ion mobility spectrometer (IMS) system, a high-performance liquid chromatography (HPLC) system, a ultra-performance liquid chromatography (UPLC®) system, a ultra-high performance liquid chromatography (UHPLC) system.

12. The computer-implemented method of claim 10, the plurality of symbols comprising binary symbols.

13. The computer-implemented method of claim 10, the at least one compound comprising a product ion and the at least one property comprising an intensity value for a precursor charge or a precursor mass-to-charge ratio.

14. The computer-implemented method of claim 10, the at least one encoded representation comprising a 128-bit string.

15. The computer-implemented method of claim 10, the at least one encoded representation comprising a primary key configured to relate a plurality of samples to the encoded representation.

16. The computer-implemented method of claim 10, the at least one segment comprising a plurality of segments, wherein at least one first segment encodes information associated with a precursor ion of the compound and at least one second segment encodes information associated with a product ion of the compound.

17. The computer-implemented method of claim 10, the at least one segment comprising at least one of a charge associated with the at least one compound in a three-bit segment, a relative time associated with the at least one compound in a ten-bit segment, or an intensity value for a mass-to-charge ratio associated with the compound in an eleven-bit segment.

18. The computer-implemented method of claim 10, comprising:
    receive second analytical information associated with a sample, and
    determine at least one ion present in the sample via a comparison of the second analytical information and the at least one encoded representation.

* * * * *